United States Patent
Sa et al.

(10) Patent No.: US 11,734,849 B2
(45) Date of Patent: Aug. 22, 2023

(54) ESTIMATING PATIENT BIOGRAPHIC DATA PARAMETERS

(71) Applicant: Siemens Healthcare GmbH, Erlangen (DE)

(72) Inventors: Ruhan Sa, Monmouth Junction, NJ (US); Birgi Tamersoy, Erlangen (DE); Yao-jen Chang, Princeton, NJ (US); Klaus Kirchberg, Plainsboro, NJ (US); Vivek Singh, Princeton, NJ (US); Ankur Kapoor, Plainsboro, NJ (US); Andreas Wimmer, Forchheim (DE)

(73) Assignee: Siemens Healthcare GmbH, Erlangen (DE)

( * ) Notice: Subject to any disclaimer, the term of this patent is extended or adjusted under 35 U.S.C. 154(b) by 105 days.

(21) Appl. No.: 16/813,859

(22) Filed: Mar. 10, 2020

(65) Prior Publication Data

US 2021/0287368 A1    Sep. 16, 2021

(51) Int. Cl.
| | |
|---|---|
| *G06K 9/00* | (2022.01) |
| *G06T 7/62* | (2017.01) |
| *G06T 7/00* | (2017.01) |
| *G16H 30/20* | (2018.01) |
| *G16H 30/40* | (2018.01) |
| *G06N 3/08* | (2023.01) |
| *G06T 5/50* | (2006.01) |
| *G06T 7/174* | (2017.01) |
| *G06T 5/00* | (2006.01) |

(Continued)

(52) U.S. Cl.
CPC ............ *G06T 7/62* (2017.01); *G06N 3/08* (2013.01); *G06T 5/002* (2013.01); *G06T 5/50* (2013.01); *G06T 7/0014* (2013.01); *G06T 7/174* (2017.01); *G06V 10/454* (2022.01); *G06V 10/82* (2022.01); *G06V 40/70* (2022.01); *G16H 30/20* (2018.01); *G16H 30/40* (2018.01); *G06N 3/04* (2013.01); *G06T 2207/20081* (2013.01); *G06T 2207/20084* (2013.01)

(58) Field of Classification Search
CPC ....... G06T 7/0014; G06T 7/174; G06T 5/002; G06T 5/50; G06T 2207/20081; G06T 2207/20084; G16H 30/20; G16H 30/40; G06N 3/08; G06N 3/04
See application file for complete search history.

(56) References Cited

U.S. PATENT DOCUMENTS

| | | | |
|---|---|---|---|
| 9,524,582 B2 | 12/2016 | Ma | |
| 10,482,607 B1 * | 11/2019 | Walters | ............... G06F 21/6254 |

(Continued)

OTHER PUBLICATIONS

Body Weight Estimation for Dose-Finding and Health Monitoring of Lying, Christian Pfitzner, Apr. 24, 2018, 23.*

(Continued)

*Primary Examiner* — Xin Jia

(57) ABSTRACT

Patient biographic data may be estimated by receiving patient image data, applying the patient image data to a machine learned model, the machine learned model trained on second patient data and trained to map the second patient data to associated biographic data using machine learned features, generating the patient biographic data based on the applying and the machine learned features, and outputting the patient biographic data. The patient biographic data may include a patient weight, a patient height, a patient gender, and a patient age.

14 Claims, 3 Drawing Sheets

(51) Int. Cl.
*G06V 10/82* (2022.01)
*G06V 10/44* (2022.01)
*G06V 40/70* (2022.01)
*G06N 3/04* (2023.01)

(56) References Cited

U.S. PATENT DOCUMENTS

| | | | | |
|---|---|---|---|---|
| 2018/0315182 | A1* | 11/2018 | Rapaka | G16H 50/70 |
| 2020/0085382 | A1* | 3/2020 | Taerum | G06V 10/764 |
| 2020/0265579 | A1* | 8/2020 | Schmidt-Richberg | |
| | | | | G06N 20/00 |
| 2021/0327563 | A1* | 10/2021 | He | G06N 3/0454 |

OTHER PUBLICATIONS

Anguelov, Dragomir, et al. "SCAPE: shape completion and animation of people." ACM transactions on graphics (TOG). vol. 24. No. 3. ACM, 2005.

Caesar "The Most Comprehensive Source for Body Measurement Data" http://store.sae.org/caesar/ Accessed Nov. 29, 2018.

Coe, T. R., et al. "The accuracy of visual estimation of weight and height in pre-operative supine patients." Anaesthesia 54.6 (1999): 582-586.

Diedler, Jennifer, et al. "Is the maximum dose of 90 mg alteplase sufficient for patients with ischemic stroke weighing 100 kg?." Stroke 42.6 (2011): 1615-1620.

Huang, Gao, et al. "Densely connected convolutional networks." Proceedings of the IEEE conference on computer vision and pattern recognition. Jan. 2018. pp. 1-9.

Menon, Shyaman, et al, "How accurate is weight estimation in the emergency department?." Emergency Medicine Australasia 17.2 (2005): 113-116.

Pfitzner, Christian, et al. "Body weight estimation for dose-finding and health monitoring of lying, standing and walking patients based on RGB-D data." Sensors 18.5 (2018): 1311. pp 1-23.

Prakash, Priyanka, et al. "Is weight-based adjustment of automatic exposure control necessary for the reduction of chest CT radiation dose?." Korean journal of radiology 11.1 (2010): 46-53.

Singh, Vivek, et al. "Darwin: Deformable patient avatar representation with deep image network." International Conference on Medical Image Computing and Computer-Assisted Intervention. Springer, Cham, 2017.

Velardo, Carmelo, et al. "Weight estimation from visual body appearance." 2010 Fourth IEEE International Conference on Biometrics: Theory, Applications and Systems (BTAS). IEEE, 2010 pp. 1-6.

Velardo, Carmelo, et al. "What can computer vision tell you about your weight?." 2012 Proceedings of the 20th European Signal Processing Conference (EUSIPCO). IEEE, 2012 pp. 1-5.

U.S. Appl. No. 16/283,864, filed Feb. 25, 2019.

* cited by examiner

ESTIMATING PATIENT BIOGRAPHIC DATA PARAMETERS

FIELD

The following disclosure relates to estimating biographic parameters of patients.

BACKGROUND

Clinically-relevant patient data may be determined in order to guide patient care. For example, biographic data (or "meta-data") such as the height, weight, age, or gender of a patient may be used to adjust a radiation dosage for medical image scanning, or a drug dosage. In some cases, the patient biographic data may not be measured directly. For example, an incapacitated patient may be unable to state their age, gender, or other patient biographic data. By one measure, only 14.6% of stroke patients are weighed, with physicians or nursing staff guessing the weight of the remaining patients. In another example, a care environment with limited resources may not be able to weigh or measure every patient.

When the biographic data is not measured directly, the biographic data may be estimated. For example, physicians, nurses, or other staff may guess a patient's weight or height. However, estimation of such biographic data may vary significantly from person to person and may deviate from the true measurement. Incorrect or inaccurate patient biographic data may result in, for example, patients receiving unnecessary or excessive radiation doses or incorrect medication doses. For example, without weight-based adjustment of exposure control for a computed tomography (CT) scan, a patient may be exposed to a 17-43% higher radiation dose.

SUMMARY

By way of introduction, the preferred embodiments described below include methods and systems for estimating patient biographic data parameters.

In a first aspect, a method for estimating patient biographic data includes receiving patient image data, applying the patient image data to a machine learned model, the machine learned model trained on second patient data and trained to map the second patient data to associated biographic data using machine learned features, generating the patient biographic data based on the applying and the machine learned features, and outputting the patient biographic data.

The patient biographic data may include one or more of a patient weight, a patient height, a patient gender, and a patient age. The patient image data may be a two-dimensional patient image or a three-dimensional patient image. The patient image data may include a plurality of patient images. In one embodiment, the plurality of patient images forms a video stream. The plurality of patient images in the video stream may be smoothed. The machine learned features may be learned as part of deep learning. In one embodiment, the learned model is a first machine learned model and the method for estimating patient biographic data includes extracting one or more machine learned features based on applying the patient image data to the first machine learning model, and applying the one or more machine learned features to a second machine learning model trained on second landmarks. Generating the patient meta data may be based on applying the one or more machine learned features to the second machine learning model. In one embodiment, the method may further include segmenting a patient body from the patient image data. Applying the patient image data to the machine learned model may include applying the patient body to the machine learned model.

In a second aspect, a method of training a machine learning model includes retrieving patient image data, storing patient biographic data associated with the patient image data, training with machine learning the machine learning model based on the patient image data and the patient biographic data, and storing the machine learned model. A result of the training may be a machine learned model configured to map the patient image data to the biographic data based on machine learned features in the patient image data.

In one embodiment, the method may include applying further patient image data to the machine learned model, generating further patient biographic data based on the applying, and outputting the further patient biographic data. Values of connection weights in the machine learning model may be initialized based on a second machine learned model. The second machine learned model may be trained to generate second patient biographic data of a different type than the patient biographic data. The patient image data may include one or more machine learned patient features extracted from the patient image data and training the machine learning model may include training with machine learning the machine learning model based on the machine learned patient features and the patient biographic data.

In a third aspect, a method for estimating patient parameters includes receiving first patient image data, applying the patient image data to a first machine learned model, the first machine learned model trained on second patient image data and configured to map the second patient image data to associated machine learned patient features, extracting machine learned patient features from the patient image data based on applying the first patient image data, applying the machine learned patient features to a second machine learned model, the first second machine learned model trained on second machine learned patient features and configured to map the second machine learned patient features to associated biographic data, generating patient biographic data based on applying the machine learned patient features, and outputting the patient biographic data.

The patient biographic may include a patient weight, patient height, patient gender, patient age, or a combination thereof. The patient image data may be a two-dimensional patient image or a three-dimensional patient image. The patient image may include a plurality of patient images. The plurality of patient images may compose a video stream. The machine learned patient features may be learned as a part of deep learning.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
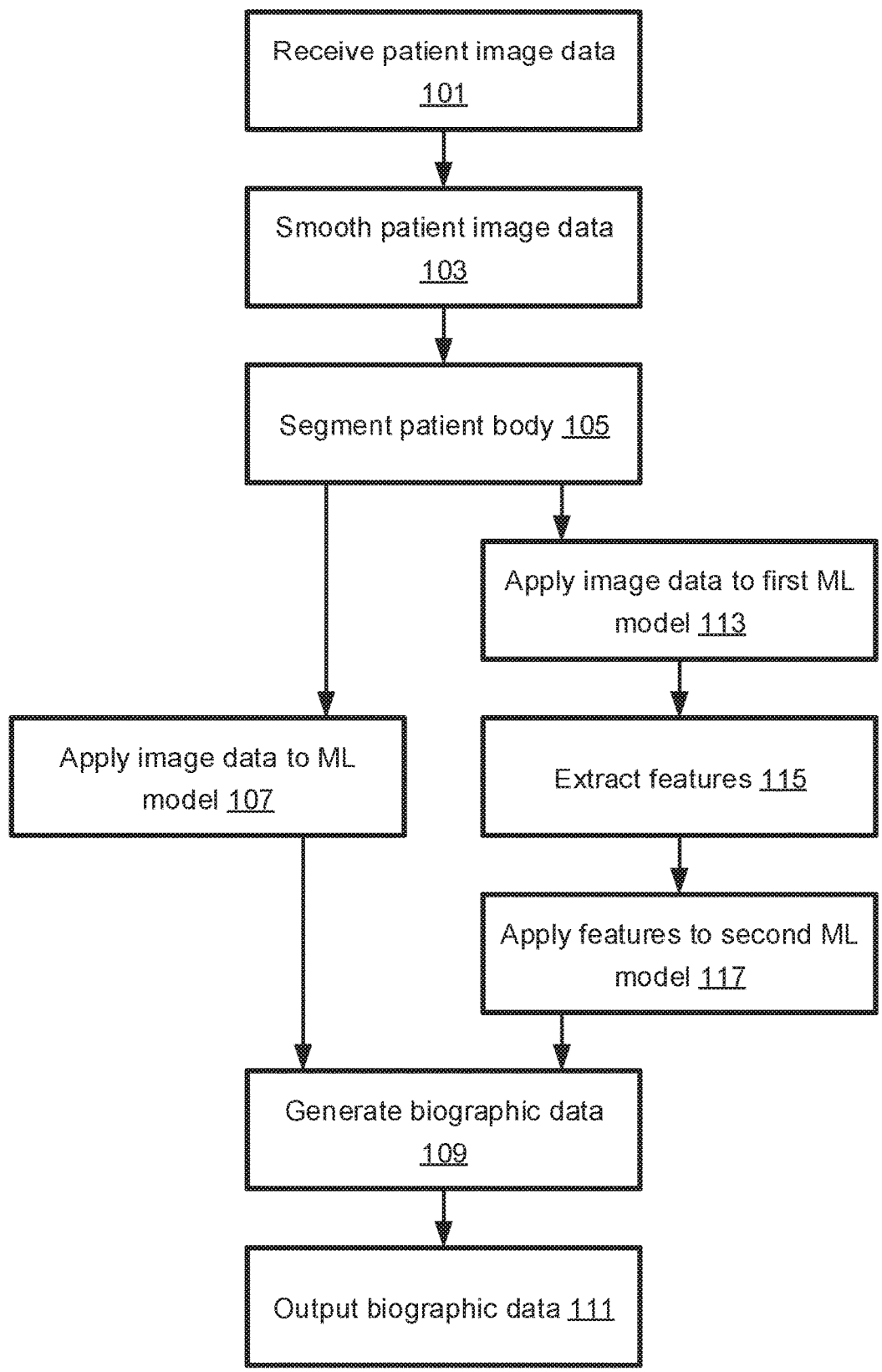
FIG. 1 illustrates an embodiment of a method for estimating patient biographic data.

In light of the difficulty of accurately estimating patient biographic data by humans, machine learning and direct calculation of biographic data using patient volume and estimated density have been used to automatically estimate patient weight previously proposed. However, the patient features, anatomic features, or landmarks used in the machine learning and direct calculation methods are manually-selected features and such methods do not estimate the biographic data directly from an underlying image of a patient.

One example of a manually-selected feature is a patient volume calculated from the patient image that may be used to estimate a weight of the patient. In some cases, a surface of the patient may be determined based on the patient image and the manually-selected features may be extracted from the surface. For example, manually-selected features may be extracted from a surface of the patient and used to estimate the weight. In a further example, a height, a length of an arm, and/or a circumference of the arm of the patient are patient features that may be extracted from the image and used to determine the weight of the patient. The patient volume, the surface data, and the measurements of the patient are manually selected features because a clinician or researcher discovers, selects, or determines the features in the patient images, and uses the features to estimate the biographic data, instead of estimating the biographic data with the patient image data natively. In each of these cases, a human operator selects which features is going to be extracted or used to estimate the biographic data. Further, the biographic data estimated using these manually selected features may be inaccurate or only accurate for a small set of patient bodies.

Instead of relying on manually selected features to estimate patient biographic data, a machine learning model may be trained to estimate the biographic data based on an input patient image and machine learned features (e.g. without manually selecting or identifying which features to use). In this way, the machine learning model may rely on "machine learned features" that are learned during training (e.g. during deep learning) to estimate the patient biographic data from the patient image. By using features that are learned during training, the machine learning model may learn or reinforce features that are the best performing for the output biographic data.

In an "end-to-end" example, one machine learned model is trained to output patient biographic data in response to an input patient image without input of a value or values of features derived from the patient image. Feature extraction may be learned during training. For example, a convolutional neural network is trained with deep learning where the machine training learns the convolution kernels or layers. Each convolutional layer of the model may correspond to or represent one or more learned features.

In a "stepwise" example, two machine learned models are used. The first machine learned model may output the machine learned features based on an input patient image. The second machine learned model may output the patient biographic data based on input machine learned features.

FIG. 1 illustrates an embodiment of a method for estimating patient biographic data. More, fewer, or different acts may be performed. In some cases, one or more of acts 103, 105, or 111 may be omitted. In some other cases, one or more of acts 113, 115, and 117 may be omitted. In still some other cases, act 107 may be omitted. The acts may be performed in a different order than shown. For example, act 113 may proceed directly from act 103. In another example, act 103 may proceed from act 105. A processor coupled to a memory may be configured to perform one or more of the acts. For example, the processor 303 and memory 305 of FIG. 3 may be configured to perform one or more of the acts of FIG. 1.

In act 101, patient image data is received. In some cases, the patient image data may be received from a remote computer or sensor, such as a depth camera. For example, the patient data may be received via the network adapter 307 of FIG. 3. In some other cases, the patient image data may be received from a local memory, storage, or sensor. For example, the patient image data may be received or retrieved from the memory 305. In another case, the patient image data is received from or within a medical scanner, such as a computed tomography, magnetic resonance, positron emission tomography, single photon emission computed tomography, ultrasound, or another modality of scanner.

The patient image data may include a representation or image of the patient. In some cases, the patient image data may include multiple images or representations of the same patient. The patient may be nude or covered with light clothing or hospital attire in the patient image data. In this way, the patient image data may include external information about the patient. In some cases, the patient may be in a particular or predefined pose in the patient image data. For example, the patient may be standing or lying down in the patient image data.

The patient image data may include one or more images of the patient. In some cases, the images may be two-dimensional or three-dimensional. For example, the images may be an RGB image, and RGB image with depth information, or a point cloud of depth information. The patient image data may be generated by a camera and/or a depth sensor. For example, the patient image data may be generated by the image sensor 309 of FIG. 3, or a remote sensor. The camera may be an RGB camera. The depth sensor may be and RGB+depth camera or a light detection and ranging (LI DAR) sensor. In some cases, the patient image data may be a video stream. The images of the patient image data may be part of or compose the video stream. For example, the images may be video frames of the video stream.

In act 103, the patient image data is smoothed. When the patient image data includes multiple patient images, the images may be processed together to remove noise. For example, stacking the images and smoothing any differences between the images may reduce noise present in the patient image data. In another example, the images may be applied to a machine learned model, such as a deep learning model, and a smoothed image may be generated based on applying the images to the model. The smoothing may be a gaussian smoothing over space and/or time. When multiple images are temporally smoothed together, a single smoothed image may result.

Additionally or alternatively, noise may be reduced in the patient image data in act 103. When the patient image data includes depth data, a range of depth data may be retained or removed from the patient image data. For example, a height of the table may be predetermined and/or determined based on the depth data. A range of the depth data including the table and space above a patient table (e.g. where the patient may be positioned) may be determined and retained in the patient image data and depth data lying outside of this range may be removed from the patient image data. For example, where the patient table is 0.5 m above the floor, any patient image data from a depth of 0.5 m to 1 m above the floor may be retained and data outside the range may be discarded. Other ranges may be used. In some cases, the noise may be reduced as part of act 105.

In act 105, the patient is segmented from the patient image data. In some cases, the patient may be the only person or subject in the patient image data. In some other cases, the patient image data may include multiple subjects (e.g., a patient bed or tools) or patients. The patient may be segmented or cropped out of the patient image data so that information about only the patient is used for estimating the biographic data. Segmenting may remove the background information or information about the other subjects or other patients from the patient image data. In this way, segmenting separates image data representing the body of the patient from the remaining data in the patient image data. In some cases, the segmenting may be performed manually. In some other cases, the segmenting may be performed automatically. For example, a person detection algorithm may be used to automatically segment the patient.

An "end-to-end" biographic data generation example may use a single machine learned model configured to accept as input a patient image and to output the patient biographic data. The end-to-end example may proceed to act 107. However, a "stepwise" biographic data generation example may use a first machine learned model configured to accept as input a patient image and to output values for one or more machine-learned patient features and a second machine learned model to accept as input the values of the features and to output the patient biographic data. The stepwise example may proceed to act 113.

With respect to the end-to-end example, in act 107, the patient image data may be applied to or input to a machine learned (ML) model. The machine learned model may have been trained on a set of patient data. The machine learned model may be trained, for example, in accordance with one or more acts of FIG. 2. In one example, the machine learned model may be trained on patient image data annotated with patient biographic data. The machine learned model may be configured to accept the patient image data as input and to output patient biographic data. In some cases, the machine learned model may be trained or configured to map input image data to associated biographic data using machine learned features. The machine learned model may be a machine learned network. For example, the machine learned model may be a neural network, such as DenseNet, convolutional neural network, or fully connected network.

In one example, the machine learned features may be abstract features present in or extracted from a layer of the machine learned model. The features may be an array of data or numbers and may not be directly interpreted (e.g. by a human operator) as corresponding to a physical feature of the patient. However, a second machine learned model (e.g. in a stepwise example) may use or decode the abstract features and output the biographic data. In some cases, the second machine learned model may map the abstract features into shape features (such as volume, area, diameter, circumference, length, width, curvature, other anthropometric measure, and/or other geometric measure in the patient image data) or location features (such as a position of a particular joint within the patient image, or the relation of the joint to other joints or anatomy).

When the body of the patient is segmented from the patient image data, the body may be applied to or input to the machine learned model. Multiple patient images of the patient image data may be applied to the machine learned model. For example, multiple patient images may be applied together at the same time (e.g. in parallel) to the machine learned model. In another example, multiple images are applied one at a time (e.g. serially) to the machine learned model. In some cases, once the patient image data is applied to the machine learned model, the end-to-end example may proceed to act 109.

With respect to the stepwise example, in act 113, the patient image data may be applied to a first machine learned model. The machine learned model may have been trained on a set of patient images or patient image data and associated values for the features. In this way, the first machine learned model may learn though regression the features to extract from the input patient image data. The first machine learned model may be trained, for example, in accordance with one or more acts of FIG. 2. The first machine learned model may be configured to accept the patient image data as input and to output values for one or more patient features or landmarks. In this way, the first machine learned model may be trained or configured to map input patient image data to associated features in the patient image data.

In some cases, the first machine learned model may be trained (or pre-trained) to extract manually-selected features from the patient image data. For example, the first machine learned model may be trained to extract shape, location, or other features from the patient image data. However, some of the features extracted by the first machine learned model may be more or less useful than other features for estimating the biographic data (e.g. by the second machine learned network). The second machine learned network, during training, may learn which features output by the first machine learning network form a good basis to estimate the biographic data. For example, the second machine learned model may assign a greater weight to features that are good predictors and assign a lesser weight (or not weight at all) to features that are poor predictors of the biographic data, thereby "selecting" through machine learning which features to use to predict the biographic data.

The first machine learned model may be a machine learned network. For example, the first machine learned model may be a neural network, such as DenseNet, convolutional neural network, or fully connected network. When the body of the patient has been segmented from the patient image data, the body may form at least part of the patient image data input to the first machine learned model. In some cases, the patient image data may include multiple patient images. In one example, multiple patient images together are input or applied to the first machine learned model in parallel or at the same time. In another example, one patient image at a time is applied to the first machine learning model.

In act 115, the patient features may be extracted from the patient image data. In some cases, the patient features may be abstract features. The extracting may be based on applying the patient image data to the first machine learned model. Values for multiple features, or a set of features, may be extracted for each patient image applied to the first machine learned model. Additionally or alternatively, the first machine learned network may output a single value for each feature that reflects each feature as extracted from multiple input patient images. The single value for multiple input patient images may "smooth" any noise in a particular patient image. Extracting the features may include measuring the machine learned features in the patient image data and outputting values for the features.

As described with respect to the end-to-end example, for example, the features in the stepwise example may be machine-learned or machine-selected shape features. Shape features may include a volume, area, diameter, circumference, length, width, curvature, other anthropometric measure, and/or other geometric measure in the patient image data. For example, a location feature may indicate a position of a particular joint within the patient image, or the relation of the joint to other joints or anatomy.

In act 117, the extracted values for the features may be applied to a second machine learned model. The second machine learned model may be configured to accept the values of the features as input and to output patient biographic data based on the features. The second machine learned model may be trained, for example, in accordance with one or more acts of FIG. 2.

In act 109, the biographic data is generated. The biographic data may include a patient weight, a patient height, a patient gender or sex, and/or a patient age. Some of the biographic data may be categorical, such as gender. Such biographic data may then be used in machine learning classifiers (e.g. classification neural networks and support vector machines) for other functions, such as segmentation, treatment system configuration, and/or landmark detection. The biographic data may be an output of the machine learned model or the second machine learned model. The biographic data may be generated based on data input to the machine learned model. For example, in the end-to-end example, the machine learning model learns to map the input patient image data to the output biographic data using machine learned features in the patient image data. In another example, for the stepwise example, the second machine learning model maps the input machine learned features to the output patient biographic data. In some cases, multiple estimates of biographic data may be generated based on multiple input patient images (or patient features of the multiple patient images). One estimation of the biographic data may be generated for each input patient image or set of associated patient features. In some other cases, one estimation of the biographic data may be made for multiple input patient images or machine learned features. The single estimation of the biographic data may reflect a smoothing of noise present in the input patient image data or features. Additionally or alternatively, the multiple output biographic data (e.g. an estimation of biographic data for each input patient image in the patient image data) may be smoothed or combined after estimation. For example, a Kalman filter or other filter may be used to combine the multiple outputs into a single biometric output.

In act 111, the biographic data is output. In some cases, the biographic data may be stored. For example, the biographic data may be output to and stored in the memory 305 of FIG. 3. In another example, the biographic data may be output and stored remotely. The biographic data may be sent to a remote computer via the network adapter 307. In some other cases, the biographic data may be displayed as the output. For example, the biographic data may be displayed on the display 311. A clinician may be able to access the biographic data from storage or view the biographic data on the display.

Figure 2:
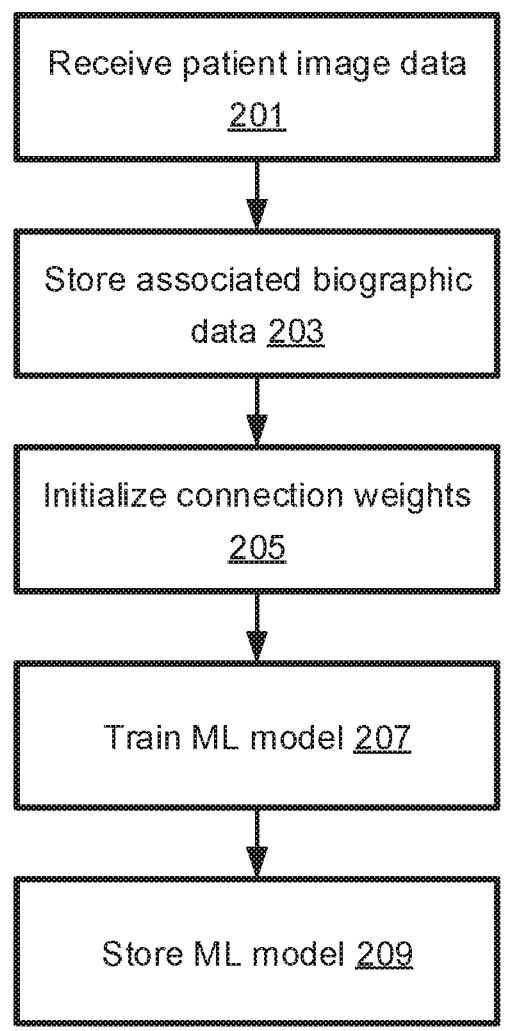
FIG. 2 illustrates an embodiment of a method for training a machine learning model in biographic parameter estimation.

FIG. 2 illustrates an embodiment of a method for training a machine learning model. More, fewer, or different acts may be performed. In some cases, act 205 may be omitted. The acts may be performed in a different order than shown. For example, act 201 may proceed directly from act 205. A processor coupled to a memory may be configured to perform one or more of the acts. For example, the processor 303 of FIG. 3 may be configured to perform one or more of the acts of FIG. 2.

In act 201, patient image data may be received. Because the patient image data may be used to train a machine learning model, the patient image data may be referred to as training image data. In some cases, the training image data may be received from a remote computer. For example, the patient data may be received via the network adapter 307 of FIG. 3. In some other cases, the training image data may be received from a local memory or storage. For example, the training image data may be received or retrieved from the memory 305. The training image data may be annotated with patient bibliographic data. For example, the training image data may contain thousands of patient images and associated bibliographic data. In this way, each patient image may have an associated patient weight, height, gender, and/or age.

In some cases, the training image data may also include patient features or landmarks identified in the patient images. The patient features may be machine learned features, meaning that a machine learned model determined which features to use and/or extracted those features from the associated patient images. In some other cases, a machine learned model may extract the patient features from the training image data. For example, where the training image data does not already have any features identified in the images, the patient features may be extracted by a machine learned model for use in training. The features may be stored as described with respect to act 203.

In some other cases, when the patient features are unknown, the patient features may be extracted from the training image data using a machine learned model. The training image data may be applied to the machine learned model trained on other training image data (e.g. not the data from act 201) that is configured to map the input training image data or patient image data to one or more machine learned features. The features (or the values of the features) may be extracted based on applying the training image data to the machine learned network. The features may be extracted using a pretrained machine learned network. For example, a machine learned network trained to regress or extract body joints (or the locations or relationships of those joints) as patient features from input patient image data may extract the features from the training image data of act 201 that may be used in act 207 to train a machine learning model. The pretrained network may decode patient visual cues in the patient image (e.g. as part of identifying bone joints) that may be useful to train a machine learning model to estimate the biographic data as well.

In act 203, biographic data associated with the training image data is stored. The biographic data may be a height, weight, age and/or gender associated with a patient image of the training image data. Each patient image in the training data may be annotated with or associated with values of one or more types of biographic data. The biographic data may be stored locally or remotely. For example, the biographic data may be stored in a remote computer (e.g. via the adapter 307) or in the memory 305. The patient images in the image data may be annotated with the biographic data. In some cases, patient features or landmarks associated with or extracted from the training image data may be stored. For example, the features (or the value of those features) may be received and stored with or as a part of the biographic data.

The patient features, and/or the associated biographic data may form the ground truth used to train the machine learning model.

In act 205, the connection weights of the machine learning model are initialized. The connection weight may be initialized based on a second, trained machine learned model. For example, initial values of the connection weights in the machine learning model (e.g. the model to be trained in act 207) may be set to the value of the connection weights of the machine learned model. In this way, the machine learning model that is to be trained is not starting "from scratch." Instead, a machine learned model configured to output one type of patient biographic data may initialize the weights of the machine learning model that is trained to output another kind of biographic data. For example, a machine learned model configured to output a patient weight may initialize connection weights for a machine learning model that will be trained to output a patient height, weight or gender. The trained machine learned model may form a starting point for the machine learning model that is trained, e.g. in act 207. Any learnable parameter, such as connections, weights for connections, convolution kernels, or variables in activation functions, may be used.

In act 207, the machine learning model is trained. The machine learning model may be trained using a machine learning technique. For example, the machine learning model may be trained using deep learning. During training for the end-to-end example, the training image data may be input or applied to the machine learning model, which outputs an estimate of biographic data for the training image data. The estimated biographic data is compared to the associated ground truth biographic data, and the machine learning model is updated based on the comparison. During training for the stepwise example, the machine learned features may be input or applied to the machine learning model, which outputs an estimate of biographic data for the machine learned features. The biographic data estimated by the machine learning model is compared to the ground truth biographic data, and the machine learning model is updated based on the comparison. For example, during training, the machine learning model may learn which applied features are a good basis for estimating the biographic data and which features are a poor basis for estimation. Successive rounds of training may reinforce the good features (e.g. by giving those features a greater weight) and de-emphasize the poor features (e.g. by giving those features little or no weight). In this way, the machine learning model automatically "selects" which input features to use to estimate the biographic data without manual selection. In some cases, the machine learned features are extracted by a machine learned model. In some other cases, the training image data is applied to a first machine learning network, which outputs values for one or more machine learned features based on the training data. The machine learned features may be applied to a second machine learning network, which outputs an estimate of the biographic data based on the features. The biographic data may be compared to the ground truth biographic data and the first machine learning model, the second machine learning model, or both the first and second machine learning models may be updated. In this way, the first machine learning network may learn which features to extract from the input image data without a user selecting or suggesting which features may be used. The features learned by the first machine learning network may be called machine learned features.

While a machine learning model may refer to the model before or during training, a "machine learned model" may refer to a model that has completed at least some training. For example, training the machine learning model may result in a machine learned model. Over multiple rounds of training, the machine learning model may more correctly estimate the biographic data for the input training image data. In this way, the machine learning model "learns" (e.g. through regression, reinforcement, or deep learning) to map the input (e.g. the patient images or the patient features) to the desired output (e.g. the associated biographic data). Once training is complete, the final or application machine-learned model is applied for unseen patients.

In some cases, for example the end-to-end example, the machine learned model may be configured to (or trained to) map the input training image data to the biographic graphic data based on one or more machine learned features. The machine learned features may be learned by the machine learning model during a training process, such as during deep learning. Different convolution layers of the machine learned model may represent or embody learned features that describes a correlation or relationship between an input patient image (or feature) and the output biographic data. In some other cases, for example the stepwise example, the machine learned model may be configured to map the input machine learned features (or the values of those features) to the biographic data.

In act 209, the machine learned model is stored. The machine learned model may be stored locally or remotely. For example, the machine learned model may be stored in a remote computer (e.g. via the adapter 307) or in the memory 305. The machine learned model may be stored for later retrieval and processing of new or unseen patient images. For example, once the machine learned model is trained, further patient images or features that were not part of the training set (e.g. the patient images of act 201) may be applied to the machine learned model and the model may be configured to output further biographic data. The machine learned model may be the model used in or may perform one or more of the acts of FIG. 1. For example, the machine learned model may be used in or may perform one or more of acts 107, 109, 113, 115, and 117.

Figure 3:
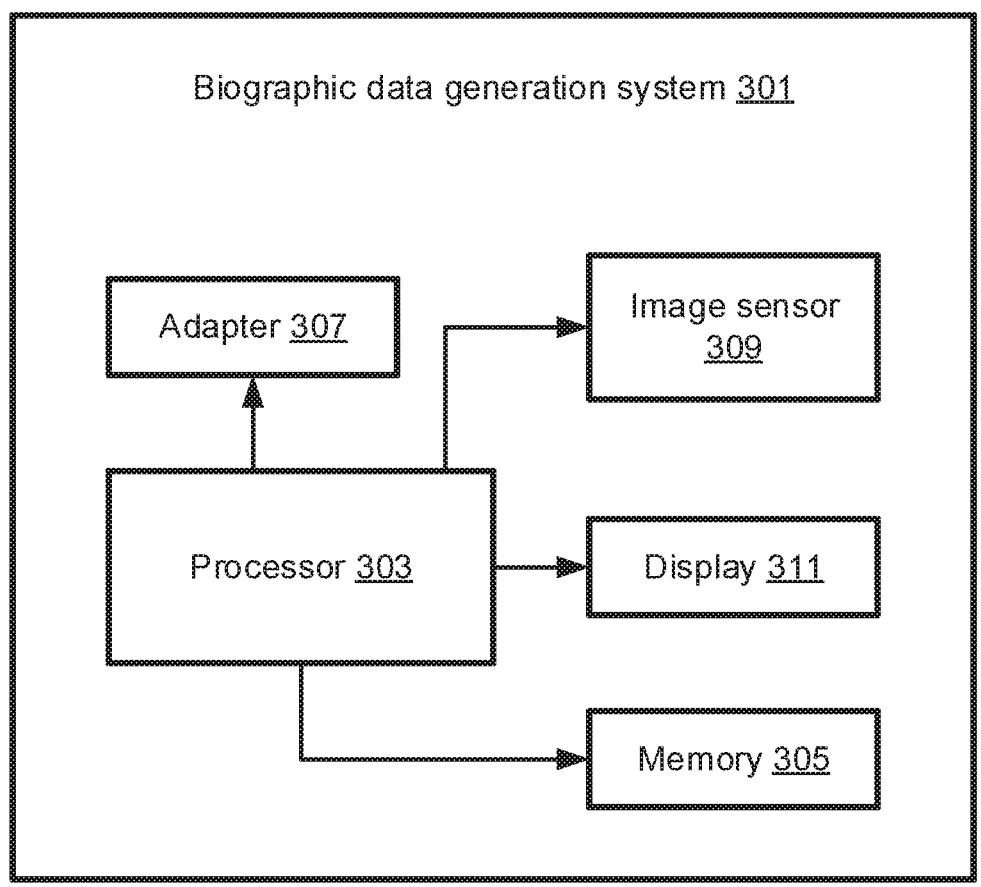
FIG. 3 illustrates an embodiment of a system for generating patient biographic data.

FIG. 3 illustrates an embodiment of a system 301 for generating patient biographic data. The system 301 may include a processor 303, memory 305, a network adapter 307, an image sensor 309, and a display 311. The display 311, processor 303, and memory 305 may be part of a medical imaging device, a computer, a server, a workstation, or another system for image processing patient image data.

Additional, different, or fewer components may be provided. For example, the image sensor 309 may be remote from the system 301. The machine learned model and the training method for the machine learning model may be applied as standalone applications on the system 301 or a local device, or as a service deployed on network (e.g. cloud) architecture. As another example, a user input device (e.g., keyboard, buttons, sliders, dials, trackball, mouse, or other device) is provided for user manipulation of the patient image data.

The processor 303 may be a controller, control processor, general processor, digital signal processor, three-dimensional data processor, graphics processing unit, application specific integrated circuit, field programmable gate array, artificial intelligence processor, digital circuit, analog circuit, combinations thereof, or other now known or later developed device for processing image data or machine learning models. The processor 303 may be a single device, a plurality of devices, or a network of devices. For more than one device, parallel or sequential division of processing may be used. Different devices making up the processor 303 may perform different functions, such as a processor for training machine learning models and another processor for generating biographic data with the machine learned models. The processor 303 may operate pursuant to and may be configured by stored instructions, hardware, and/or firmware to perform various acts described herein. For example, the acts of FIGS. 1 and 2 may be stored as instructions and configure the processor 303 to perform or execute the acts of FIGS. 1 and 2.

The memory 305 may be an external storage device, RAM, ROM, database, and/or a local memory (e.g. a solid state drive or a hard drive). The same or different non-transitory computer readable media may be used for the instructions and other data. The memory 305 may be implemented using a database management system (DBMS) and may reside on a memory, such as a hard disk, RAM, or removable media. Additionally or alternatively, the memory 305 may be internal to the processor 303 (e.g. a cache). The memory 305 may store the patient image data, features, biographic data, machine learning models, machine learned models, and/or computer program instructions. The data stored in the memory 305 may be accessible and retrievable by the processor 303 or another processor.

The instructions for implementing the model training or biographic data generation processes, the methods, and/or the techniques discussed herein may be provided on non-transitory computer-readable storage media or memories, such as a cache, buffer, RAM, removable media, hard drive or other computer readable storage media (e.g., the memory 305). Computer readable storage media may include various types of volatile and nonvolatile storage media. The functions, acts, or techniques illustrated in the Figures or described herein may be executed in response to one or more sets of instructions stored in or on computer readable storage media. The functions, acts, or techniques may be independent of the particular type of instructions set, storage media, processor or processing strategy and may be performed by software, hardware, integrated circuits, firmware, micro code and the like, operating alone or in combination.

In one embodiment, the instructions may be stored on a removable media device for reading by local or remote systems. In other embodiments, the instructions may be stored in a remote location, for example, for transfer through a computer network. In yet other embodiments, the instructions may be stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

The network adapter 307 may be in communication with one or more wired or wireless networks. Via the adapter 307, data may be sent and received between the system 301 and other computers on the network. For example, patient image data may be retrieved from a remote computer (or remote storage) via the adapter 307. In another example, generated biographic data may be sent to a remote computer (e.g. for storage or further processing) via the adapter 307.

The image sensor 309 may be a camera or depth sensor. For example, an RGB, RGB+depth, LIDAR, 2.5D, stereoscopic optical sensor, or another image sensor may be used. Though one sensor 309 is shown, multiple sensors 309 may be provided. The image sensor 309 may be directed at the patient. In this way, the image data captured by the image sensor 309 includes patient image data. The image data captured by the image sensor 309 may be stored. For example, the image data may be stored in the memory 305 or in storage remote from the system 301. In some cases, the image sensor may be part of, connected to, or disposed on a medical imaging device. The medical imaging device may be an x-ray, MRI, CAT, ultrasound, PET, or other medical imaging device.

The display 311 may be a CRT, LCD, projector, plasma, printer, tablet, smart phone or other now known or later developed display device for displaying the output, such as patient biographic data. In some cases, the display 311 may present visual or audiovisual output.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for estimating patient biographic data, the method comprising:
   receiving, by a processor, patient image data;
   applying, by the processor, the patient image data directly to a machine learned model, the machine learned model trained on second patient data and trained to map the second patient data to associated data using machine learned features, wherein during training of the machine learned model the machine learned features that map the patient image data to the associated biographic data are determined automatically by the machine learned model without manually selecting or identifying which patient features to use, wherein each convolutional layer of the machine learned model represents a learned feature that describes a correlation between input patient image data and a target output biographic data;
   generating, by the processor, the patient biographic data based on the applying and the machine learned features; and
   outputting, by the processor, the patient biographic data.

2. The method of claim 1, wherein the patient biographic data comprises one or more of a patient weight, a patient height, a patient gender, and a patient age.

3. The method of claim 1, wherein the patient image data is a two-dimensional patient image or a three-dimensional patient image.

4. The method of claim 1, wherein the patient image data comprises a plurality of patient images.

5. The method of claim 4, wherein the plurality of patient images forms a video stream.

6. The method of claim 5, further comprising:
   smoothing, by the processor, the plurality of patient images in the video stream.

7. The method of claim 1, wherein the machine learned features are learned as part of deep learning.

8. The method of claim 1, further comprising:
   segmenting, by the processor, a patient body from the patient image data, wherein applying the patient image data to the machine learned model comprises applying the patient body to the machine learned model.

9. A method for estimating patient parameters, the method comprising:
   receiving, by a processor, first patient image data;
   applying, by the processor, the first patient image data to a first machine learned model, the first machine learned model trained on second patient image data and configured to map the second patient image data to associated machine learned patient features, wherein during training of the machine learned model the machine learned features are determined automatically by the machine learned model;

extracting, by the processor, machine learned patient features from the first patient image data based on applying the first patient image data;

applying, by the processor, the machine learned patient features to a second machine learned model, the second machine learned model trained end to end with the first machine learned model in order to map one or more of the second machine learned patient features to associated biographic data without manually selecting or identifying which patient features to use;

generating, by the processor, patient biographic data based on applying the machine learned patient features; and outputting, by the processor, the patient biographic data.

10. The method of claim 9, wherein the patient biographic comprises a patient weight, patient height, patient gender, patient age, or a combination thereof.

11. The method of claim 9, wherein the first patient image data is a two-dimensional patient image or a three-dimensional patient image.

12. The method of claim 9, wherein the first patient image data includes a plurality of patient images.

13. The method of claim 12, wherein the plurality of patient images composes a video stream.

14. The method of claim 9, wherein the machine learned patient features are learned as a part of deep learning.

* * * * *